(12) United States Patent
Sugano et al.

(10) Patent No.: US 6,695,956 B2
(45) Date of Patent: Feb. 24, 2004

(54) OXYGEN CONCENTRATING APPARATUS

(75) Inventors: Masato Sugano, Tokyo (JP); Sadakazu Matsubara, Tokyo (JP); Satoshi Takaichi, Tokyo (JP)

(73) Assignee: Teijin Limited, Osaka (JP)

( * ) Notice: Subject to any disclaimer, the term of this patent is extended or adjusted under 35 U.S.C. 154(b) by 230 days.

(21) Appl. No.: 10/009,814

(22) PCT Filed: Apr. 13, 2001

(86) PCT No.: PCT/JP01/03207
§ 371 (c)(1),
(2), (4) Date: Dec. 14, 2001

(87) PCT Pub. No.: WO01/78820
PCT Pub. Date: Oct. 25, 2001

(65) Prior Publication Data
US 2003/0012704 A1 Jan. 16, 2003

(51) Int. Cl.[7] ............................................. B01D 50/00
(52) U.S. Cl. ...................... 204/265; 204/266; 205/765
(58) Field of Search ...................... 205/765; 204/265, 204/266

(56) References Cited

U.S. PATENT DOCUMENTS 5,053,116 A * 10/1991 Mayer .......................... 204/406
5,879,826 A * 3/1999 Lehman et al. ............... 429/13
6,544,404 B1 * 4/2003 Mazanec et al. ............. 205/765

* cited by examiner

*Primary Examiner*—Arun S. Phasge
(74) *Attorney, Agent, or Firm*—Rader, Fishman & Grauer PLLC

(57) ABSTRACT

An oxygen-concentrating equipment comprising an oxygen-concentrating means for separating oxygen from air and concentrating the oxygen, a humidifying means for humidifying the oxygen-concentrated air produced by said oxygen-concentrating means, and an oxygen-supplying means for supplying the humidified oxygen-concentrated air to a user, characterized in that said humidifying means has at least a cation-conducting solid electrolyte membrane equipped with electrodes on both the sides of the membrane and an electric source for applying an electric current to said electrodes.

9 Claims, 7 Drawing Sheets

OXYGEN CONCENTRATING APPARATUS

TECHNICAL FIELD

The present invention relates to a medical oxygen-concentrating equipment for separating oxygen from air and producing the oxygen-concentrated air. In more detail, the invention relates to an oxygen-concentrating equipment in which a humidifying means using a solid electrolyte membrane to humidify the oxygen-concentrated air is installed, and to the medical oxygen-concentrating equipment with which a user can continuously inhale oxygen without supplying water.

BACKGROUND ART

A medical gas including oxygen is supplied in the form of a compressed gas in a cylinder, a liquefied gas in a cylinder or direct supplying from a purifying-concentrating equipment. Among them, the concentrating equipment includes equipments based on a low temperature processing method, equipments based on a membrane separation method using a membrane permitting the preferential penetration of only a specific gas component, and equipments based on an adsorption method using an adsorbent such as zeolite. However, as the oxygen-concentrating equipments used in hospitals or by patients at their homes, the equipments based on the adsorption method, especially a pressure swing adsorption method that the inner pressure of an adsorption cylinder filled with a nitrogen-adsorbing agent based on zeolite is continuously changed to carry out adsorption and reactivation operations, are dominant.

The adsorbent used for the pressure swing adsorption method includes zeolite and molecular sieve carbon, but the equipment using 5A type or 13x type zeolite is a leading one as the oxygen-concentrating equipment. These zeolites have properties for more preferentially adsorbing nitrogen than oxygen. When air is charged into the cylinder in an adsorption process, only nitrogen is selectively adsorbed to leave oxygen as a gas phase component, and the left gas is taken out to obtain the oxygen-concentrated air.

Furthermore, these zeolites have a property for adsorbing water stronger than oxygen and nitrogen. When the water is contained in air, the zeolite adsorbs the water, and the nitrogen-adsorbing capacity of the zeolite is thereby reduced to cause the deterioration of the adsorbent. When the oxygen is concentrated by the pressure swing adsorption method using the zeolite, it is therefore preferable that the air used as the raw material is in a state that the water is removed as much as possible.

On the other hand, the oxygen purified with the above-mentioned pressure swing type adsorption equipment is in an absolutely dry state that water is nearly perfectly removed by the water-absorbing property of the zeolite. When a patient inhales the absolutely dry medical gas, troubles such as the decrease in the ciliary movement of an upper respiratory tract mucous membrane, the loss of water and calorie in the body and the difficulty of expectoration due to the dryness of sputum are caused. It is therefore necessary that the medical gas is preliminarily humidified with a humidifier or the like, before the patient inhales the medical gas.

Conventionally, the humidifiers based on a method that the product oxygen gas is passed through purified water placed in a container, and based on a method that the oxygen is passed through water in a bubble state, have been often used as humidifiers for humidifying the product oxygen gas. However, since using the water, the humidifiers have problems, for example, the necessity of maintenance such as the periodical supply or exchange of the water because of the propagation of bacteria on the employment of the humidifiers for long periods, and the abnormal supply of the product oxygen gas due to the failure of reassembly on the maintenance.

As one of methods for solving the problems, a method, comprising using a water-transferring membrane, allowing raw material air to flow on one side of the membrane to transfer oxygen to the other side, simultaneously transferring moisture in the raw material air to the product oxygen by the utilization of a steam partial pressure difference, thereby dehumidifying the raw material air and simultaneously humidifying the oxygen, such as an invention described in JPA 2-99113 (1990) (hereinafter, JPA means Japanese Unexamined Patent Publication), is known. Since the humidification degree of the oxygen largely depends on the humidity of the raw material air, the method has the following problems. For example, when the humidity of the raw material air is low, the oxygen is sufficiently not humidified, while when the humidity is high, the oxygen is excessively humidified, thus forming dew on the inner surface of piping and giving unpleasantness to a patient on his inhalation of the moisture in the form of liquid water.

In addition, a method comprising by-passing the water transfer membrane with disposing a by-pass on a piping for the raw material air or the product oxygen, in such oxygen-concentrating equipments described in JPA 5-49697 (1993) and JPA 8-196635 (1996), has also been considered for controlling the humidification degree. However, the method has problems such as the complication of the piping and the complication of a control mechanism due to a necessity for controlling the valve aperture of the by-bass for the control of the humidification degree.

Recently, a dehumidifier using a cation-conducting solid polymer electrolyte, as described in JPA 0-223220 (1998), was proposed. The dehumidifier has a basic structure having a cathode on one side of a cation-conducting solid polymer electrolyte and an anode on the other side, as shown in FIG. 6, and utilizes the following reactions:

on the side of the anode:

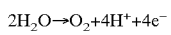
$$2H_2O \rightarrow O_2 + 4H^+ + 4e^-$$

on the side of the cathode:

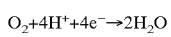
$$O_2 + 4H^+ + 4e^- \rightarrow 2H_2O$$

which are generated on the anode and the cathode, when an electric current is applied. The dehumidifier using the solid polymer electrolyte has a defect which comprises producing a dry air layer in the neighborhood of the anode side membrane surface of the solid polymer electrolyte membrane to prevent the supply of wet air to the membrane surface and thereby significantly deteriorating the humidifying capacity of the solid polymer electrolyte membrane, when continuously used.

DISCLOSURE OF THE INVENTION

The object of the present invention is to provide an oxygen-concentrating equipment installed with a humidifying means, which can dissolve the problems of conventional equipments, does not need periodical maintenance such as the supply of water, can continuously give a sufficient humidification degree, and enables the free and easy setting of the humidification degree.

The present inventor zealously examined the problem, and consequently found out the following oxygen-concentrating equipment.

Namely, the present invention is to provide the oxygen-concentrating equipment comprising an oxygen-concentrating means for separating oxygen from air to concentrate the oxygen, a humidifying means for humidifying the oxygen-concentrated air produced by said oxygen-concentrating means, and an oxygen-supplying means for supplying the humidified oxygen-concentrated air to a user, characterized in that said humidifying means has at least a cation-conducting solid electrolyte membrane equipped with electrodes on both the sides of the membrane and an electric source for applying an electric current to said electrodes.

Furthermore, the present invention is to provide the oxygen-concentrating equipment, characterized in that said humidifying means is a means which has, on the anode side, a catalyst layer for electrolyzing water molecule into oxygen molecule and hydrogen ion and has, on the cathode side, a catalyst layer for producing water molecule from the oxygen molecule and the hydrogen ion.

Furthermore, the present invention is to provide the oxygen-concentrating equipment, characterized in that said oxygen-concentrating means is a pressure swing adsorption type oxygen-concentrating means which has an adsorption cylinder filled with an adsorbent adsorbing nitrogen more selectively than oxygen and a compressor for supplying compressed air to said adsorption cylinder, and said humidifying means has a flow path to flow raw material air, to be supplied to said compressor, on an anode side and a flow path to flow the oxygen-concentrated air, produced by said oxygen-concentrating means, on a cathode side.

Furthermore, the present invention is to provide the oxygen-concentrating equipment, characterized in that said oxygen-concentrating means is a pressure swing adsorption type oxygen-concentrating means which has an adsorption cylinder filled with an adsorbent adsorbing nitrogen more selectively than oxygen and a compressor for supplying compressed air to said adsorption cylinder, and said humidifying means has a flow path to flow cooling air on an anode for cooling the inside of said oxygen-concentrating equipment and a flow path to flow the oxygen-concentrated air, produced by said oxygen-concentrating means, on a cathode side for allowing.

Furthermore, the present invention is to provide the oxygen-concentrating equipment, characterized in that said oxygen-concentrating means is a pressure swing adsorption type oxygen-concentrating means which has an adsorption cylinder filled with an adsorbent adsorbing nitrogen more selectively than oxygen and a compressor for supplying compressed air to said adsorption cylinder, and said humidifying means has a flow path to flow the air desorbed from the adsorption cylinder on an anode side and a flow path to flow the oxygen-concentrated air, produced by said oxygen-concentrating means, on a cathode side.

Furthermore, the present invention is to provide the oxygen-concentrating equipment, characterized in that a control means, for controlling the electric current value and/or voltage value of an electric current applied from said electric source to said electrodes, is installed and in that a control means, for controlling the electric current value and/or voltage value of an electric current applied from said electric source to said electrodes so that the electric current value and/or voltage value do not exceed the upper limits, is installed.

Furthermore, the present invention is to provide the oxygen-concentrating equipment, characterized in that a humidity-measuring means, on the cathode side of said humidifying means or in the downstream on the cathode side of said humidifying means, is installed and a control means, for controlling said measuring means so that the measurement value of said humidity-measuring means is equal to a set value, is installed and in that a control means, for calculating the transfer rate of water on the basis of the flow rate value and temperature value of the oxygen-concentrated air flowing on the cathode side of said humidifying means and then controlling said control means, is installed.

Figure 1:
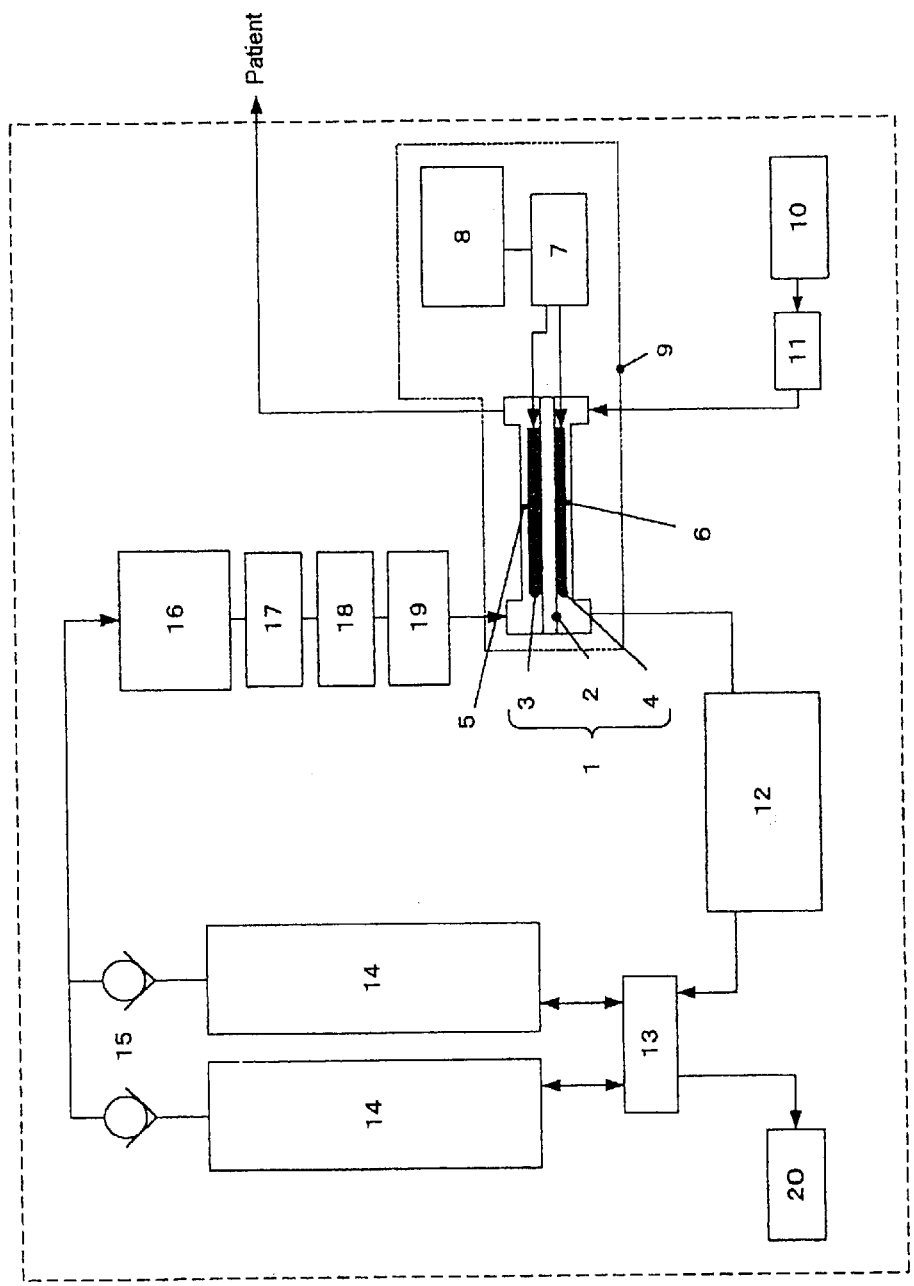
FIG. 1 is an outline flow figure of an oxygen-concentrating equipment in an embodiment of the present invention.

The marks in Figures mean as follows, respectively.
1. Solid polymer electrolysis element
2. Solid polymer electrolysis membrane
3. Cathode
4. Anode
5. Flow path on the cathode side
6. Flow path on the anode side
7. Direct electric current source
8. Humidification degree control means
9. Humidification means (humidification-dehumidification means)
10. Inspiration filter
11. Silencer
12. Compressor
13. Switch valve
14. Adsorption cylinder
15. Check valve (back-flow inhibition valve)
16. Product tank
17. Pressure control valve
18. Flow rate setter
19. Product filter
20. Silencer
21. Housing of the oxygen-concentrating equipment
22. Electric current control means
23. Humidity sensor 24. Dial for setting the humidification degree
25. Flow rate sensor
26. Temperature sensor
27. Means for controlling the upper limit of the electric current
28. Means for controlling the upper limit of the voltage.

BEST MODE FOR CARRYING OUT THE INVENTION

The oxygen-concentrating equipment in the present invention is an oxygen-concentrating equipment comprising an oxygen-concentrating means for separating oxygen from air to concentrate the oxygen, a humidifying means for humidifying the oxygen-concentrated air produced by said oxygen-concentrating means, and an oxygen-supplying means for supplying the humidified oxygen-concentrated air to a user, wherein said humidifying means has at least a cation-conducting solid electrolyte membrane equipped with electrodes on both the sides of the membrane and an electric source for applying an electric current to said electrodes.

The humidifying means is preferably a means which has, on the anode side, a catalyst layer for electrolyzing hydrogen molecule into oxygen molecule and hydrogen ion and has, on the cathode side, a catalyst layer for producing water molecule from the oxygen molecule and the hydrogen ion, and the material, that is distributed three-dimensionally with a platinum group metal such as platinum, platinum-carried carbon, ruthenium, indium, or palladium, or their oxides on the surfaces of a cation-conducting solid electrolyte membrane and on the cathode side and the anode side, may concretely be applied. A membrane such as NAFION-117 produced by du Pont Co. may be used as the cation-conducting solid electrolyte membrane.

When an electric current is applied to the solid polymer electrolysis element which is the cation-conducting solid electrolytic membrane equipped with the electrodes on both the sides of the membrane, the oxygen produced on the anode side is released in the gas on the anode side, and the electrons are transferred from the anode to the electric source via a wiring. The hydrogen ions are transferred to the cathode side through the membrane. On the cathode side, water molecule is produced from the hydrogen ions penetrated from the anode side, the electrons transferred from the electric source, and the oxygen in the gas on the cathode side, and then released in the gas on the cathode side. Consequently, on the anode side, the oxygen is produced and the gas is simultaneously dehumidified, while the oxygen is consumed to humidify the gas on the cathode side.

FIG. 1 shows the concrete embodiment of the oxygen-concentrating equipment of the present invention. Raw material air, at first, is taken in from outside air via an inspiration filter 10 and a silencer 11, and flowed through the anode side flow path 6 of a solid polymer electrolysis element 1. The raw material air is dehumidified and simultaneously concentrated with oxygen there, pressurized with a compressor 12, and then guided into adsorption cylinders 14 via a switch valve 13. The product oxygen is taken out from the opposite side of the adsorption cylinder, and then once stored in a product tank 16 via a check valve 15. The product oxygen is further flowed through the anode side flow path 5 of the solid polymer electrolysis element via a pressure control valve 17, a flow rate setter 18, and a product filter 19. The product oxygen is humidified in the anode side flow path. The humidified oxygen is supplied to a patient via a pipe means.

The characteristic of this method is to improve the total efficiency of the adsorption device, because the raw material air is dehumidified and also because the oxygen consumed on the humidification of the oxygen is returned to the side of the raw material air and recycled. Furthermore, the problems of the dehumidifier, such as a problem, that the humidifying capacity is remarkably reduced, because the generation of a dry air layer in the neighborhood of the anode side membrane surface of the solid polymer electrolyte membrane on the continuous operation is generated to obstruct the supply of wet air to the membrane surface, can be dissolved by always flowing the raw material air and the product oxygen gas especially even without disposing a ventilation means or the like, in the oxygen-concentrating equipment of the present invention.

Figure 2:
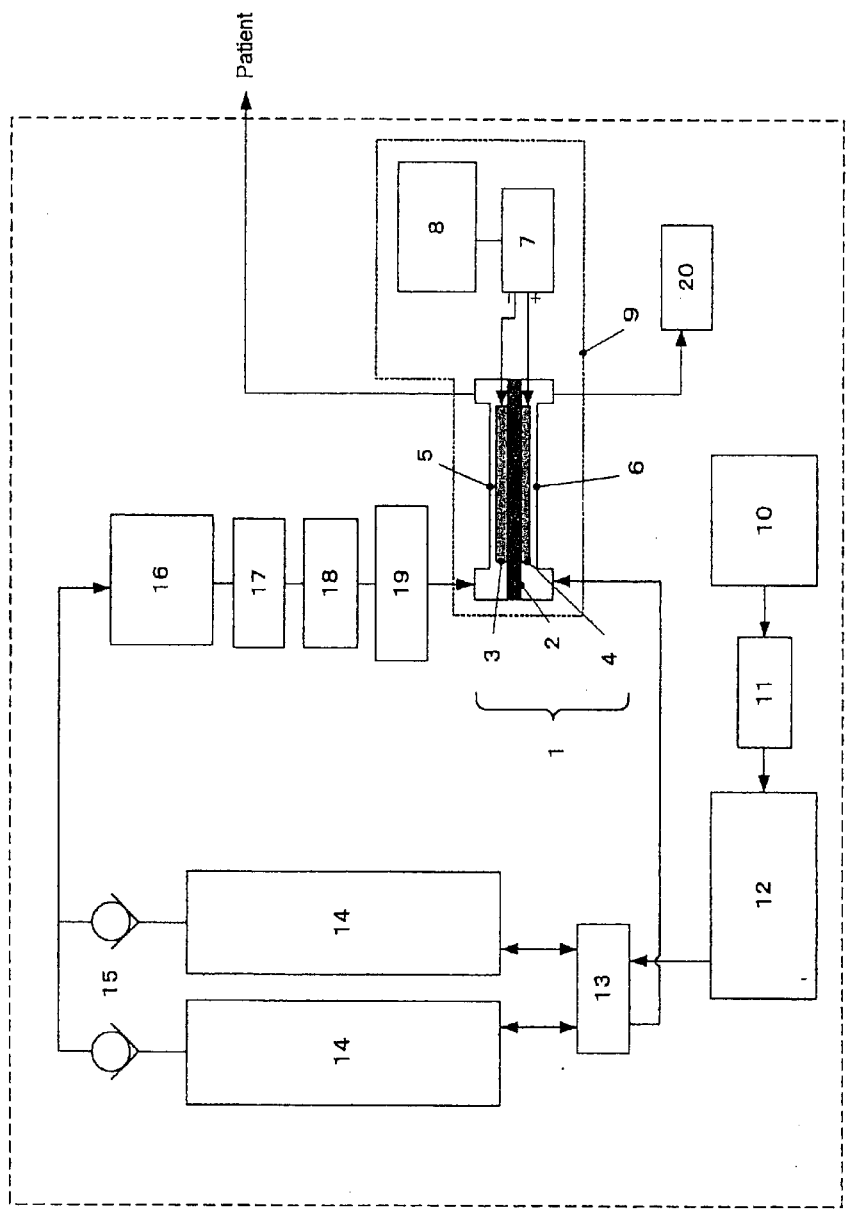
FIG. 2 is an outline flow figure of an oxygen-concentrating equipment in the other embodiment of the present invention.

FIG. 2 shows the second concrete embodiment of the oxygen-concentrating equipment of the present invention. Raw material air is taken in from outside air via an inspiration filter 10 and a silencer 11, pressurized in a compressor 12, and then supplied to adsorption cylinders 14 via a switch valve 13. In a process for reactivating the adsorption cylinders, the switch valve 13 is switched to guide the exhaust gas plentifully containing moisture from the adsorption cylinders 14 to the anode side flow path 6 of the solid polymer electrolysis element 1 via the switch value 13, and then exhausted via a silencer 20. On the other hand, oxygen taken out from the opposite sides of the adsorption cylinders 14 is humidified in the same process as in the first embodiment and then is supplied to a patient. Since the gas exhausted in the process for reactivating the adsorption cylinders is a gas from which the dry oxygen is taken out, the exhausted gas contains moisture plentifully. Thereby, this method has an advantage for improving the humidifying capacity of the solid polymer electrolysis element, because the gas plentifully containing the moisture is supplied to the anode side of the solid polymer electrolysis element.

Figure 3:
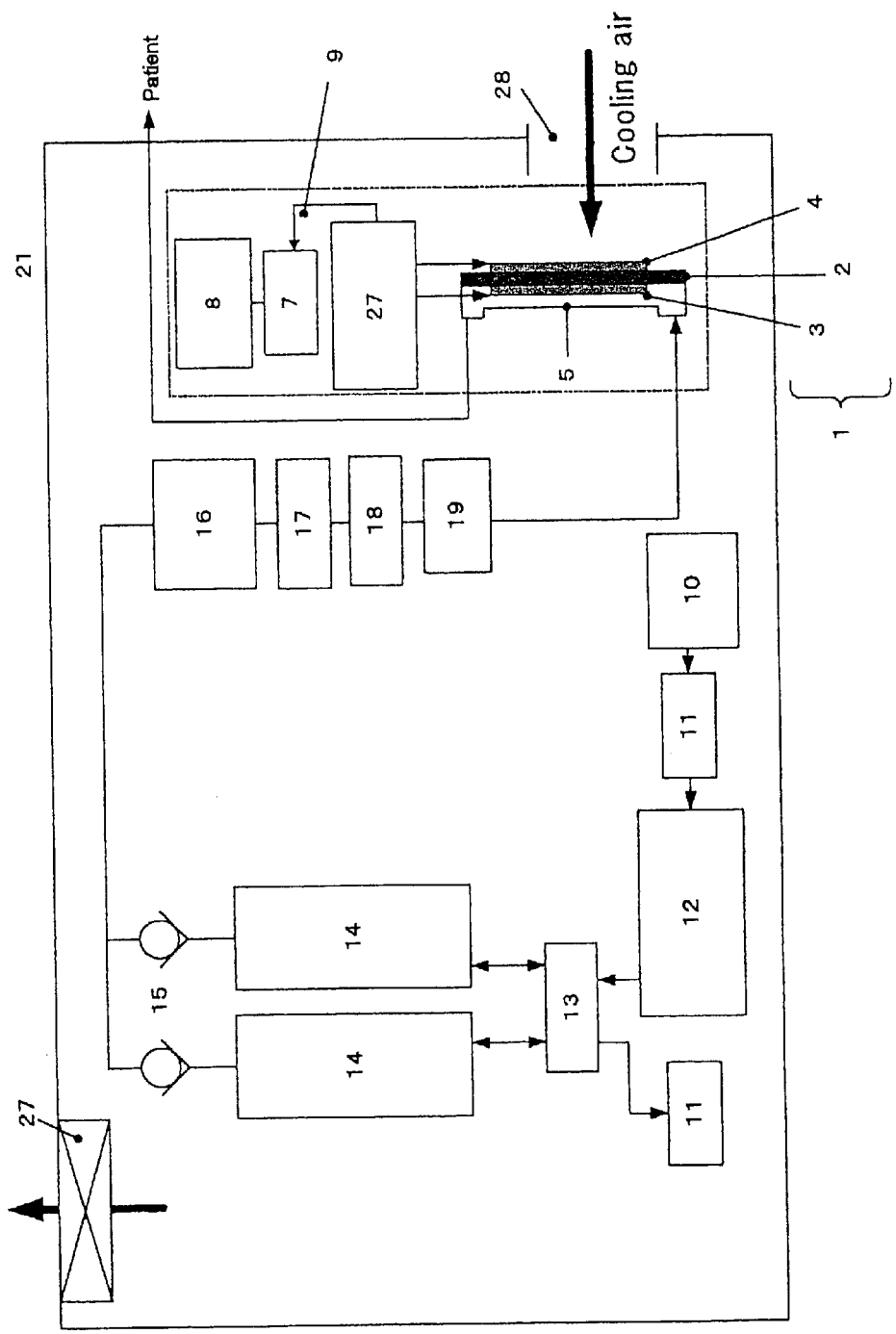
FIG. 3 is an outline flow figure of an oxygen-concentrating equipment in the other embodiment of the present invention.

FIG. 3 shows the third concrete embodiment of the oxygen-concentrating equipment of the present invention. A humidification means 9 is placed at an arbitrary place in the housing 21 of the oxygen-concentrating equipment, and the anode side of a solid polymer electrolysis element 1 is opened in said housing. Since the inside of the housing is always ventilated to cool the inside, the dehumidified air is not stayed in the neighborhood of the anode. Since not limiting the position of the humidification means disposed in the housing, this method is effective in the case of simple humidification. But, it is preferable to dispose the humidification means at an air flow-rich place in the housing, because the humidification capacity of the humidification means is improved with the increase of ventilation at a place near to the anode.

Figure 4:
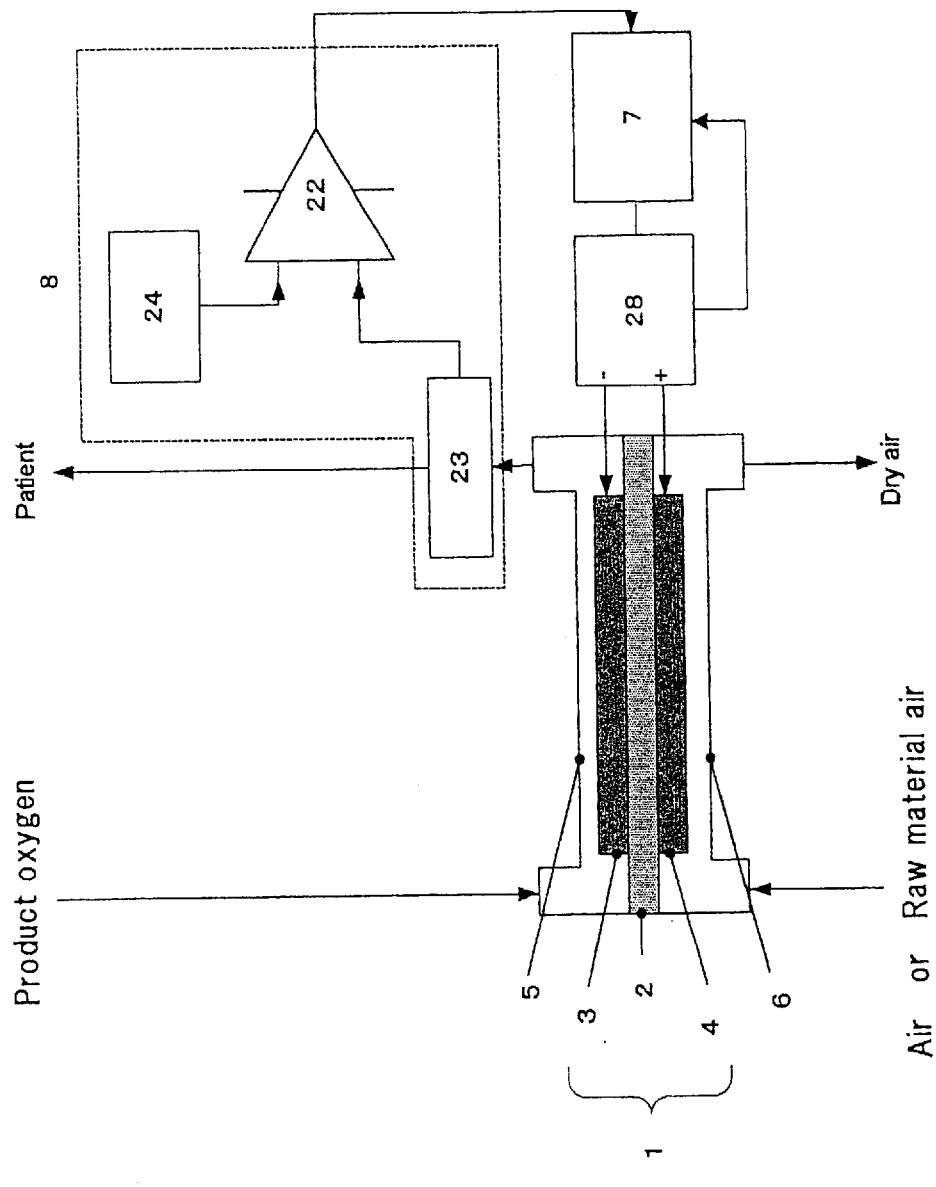
FIG. 4 is an embodiment which shows a method for controlling the oxygen humidification degree of the oxygen-concentrating equipment of the present invention and a means for the same control.

FIG. 4 shows the first concrete embodiment of a method for controlling an oxygen-humidification degree in the oxygen-concentrating equipment of the present invention. The product oxygen is supplied to a patient via the cathode side flow path 5 of a solid polymer electrolysis element 1 and a pipe. An electric current flowing from the anode 4 of the solid polymer electrolysis element 1 to the cathode 3 is supplied from an electric source, and the current value is controlled by a humidification control means. The humidification control means comprises a humidity sensor 23 disposed on the downstream side of the cathode side flow path 5, a humidity-setting dial 24 and an electric current control means 22. The actions of the electric current control means comprises comparing a signal from the humidity sensor 23 with the signal of a set humidity set with the humidity-setting dial 24 and then increasing an electric current flowing in the solid polymer electrolysis element 1, when the humidity value measured with the sensor is lower than the set humidity value, or adversely decreasing the electric current flowing in said element, when the measured humidity value is higher than the set humidity value Consequently, this electric current control means automatically controls the electric current value so that the optimal electric current for humidifying the product oxygen to the set humidity flows in the element.

Figure 5:
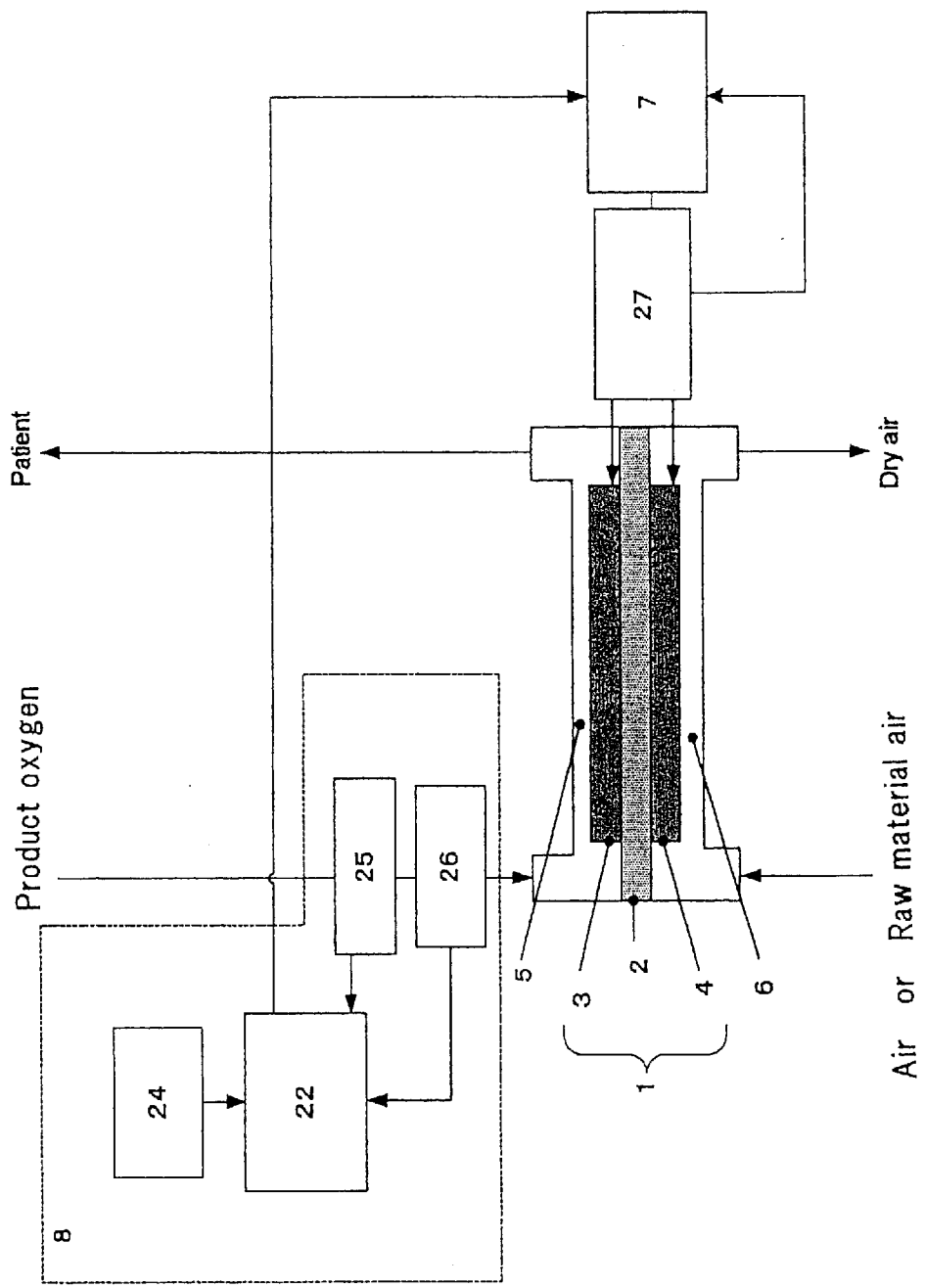
FIG. 5 is an embodiment which shows a method for controlling the oxygen humidification degree of the oxygen-concentrating equipment of the present invention and a means for the same control.
Figure 6:
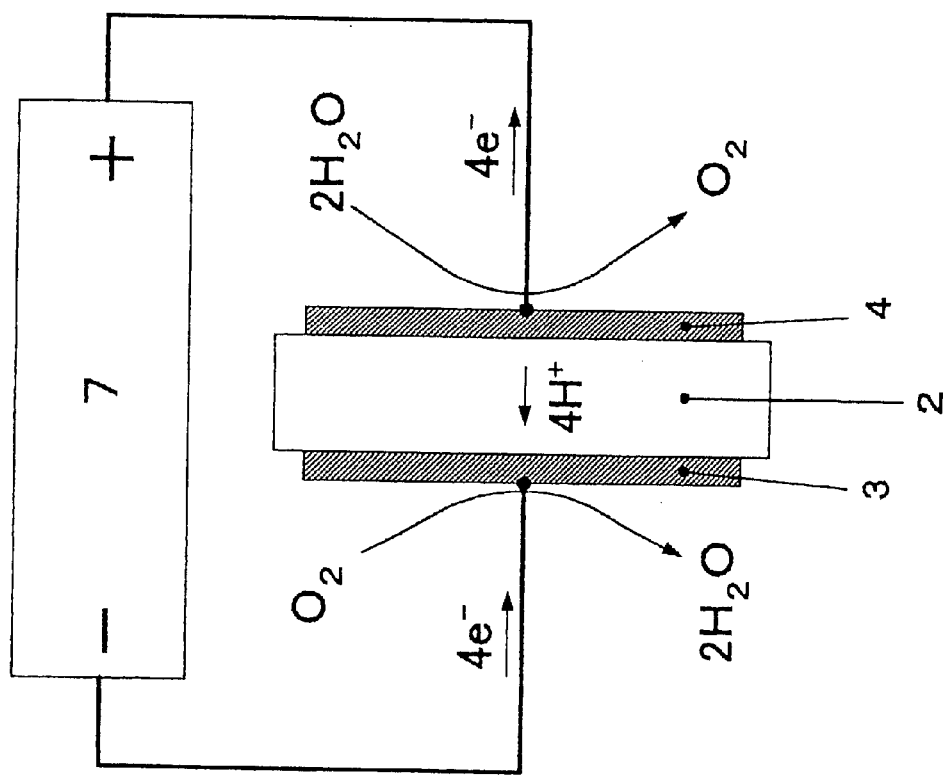
FIG. 6 is the basic structure figure of the humidifying means element installed with the solid polymer electrolyte membrane used in the oxygen-concentrating equipment of the present invention.

FIG. 5 shows the second concrete embodiment of the method for controlling the oxygen-humidification degree in the oxygen-concentrating equipment of the present invention. A humidification degree control means 8 comprises a humidity-setting dial 24, an electric current control means 22, a flow rate sensor 25 for measuring the flow rate of the product oxygen, and a temperature sensor 26 for measuring the temperature of the product oxygen. The product oxygen is flowed in the cathode side flow path 5 of the solid polymer electrolysis element 1 via the flow rate sensor 25 and the temperature sensor 26. The electric current control means 22 calculates the necessary magnitude of an electric current from the signals of the flow rate sensor 25 and the temperature sensor 26 and then controls the value of electric current flowing in the solid polymer electrolysis element 1.

Figure 7:
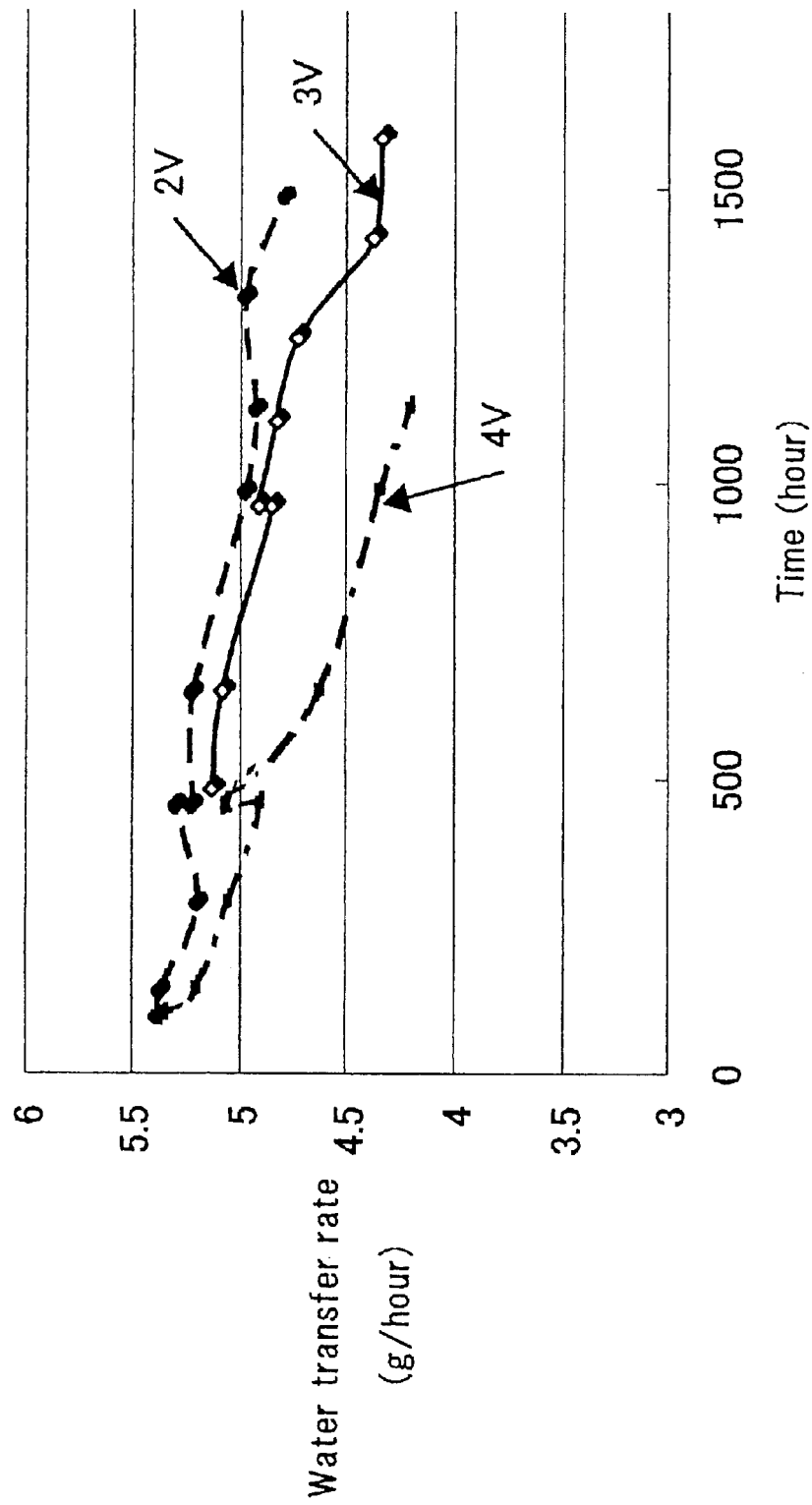
FIG. 7 is a measurement example which shows the performance deterioration of the solid polymer electrolyte membrane used in the oxygen-concentrating equipment of the present invention.

FIG. 7 shows the deterioration characteristics of the solid polymer electrolysis element 1, when used for a long period. The axis of ordinate is the rate of water which really passes through the solid polymer electrolysis element and humidifies the oxygen. It can be understood that the deterioration of the solid polymer electrolysis element 1 is accelerated with the enhancement in the value of the applied voltage. In order to prevent the deterioration of the solid polymer electrolysis element, it is thereby preferable to control the voltage at 4 V or below. The life of the solid polymer electrolysis element 1 can be elongated by considering a voltage for initiating the electrolysis of water, setting the upper limit of the voltage within a range of 0 to 4 V, preferably 2 to 3 V, and by feeding back the voltage to the electric current source 7 via a voltage upper limit value-controlling means. The life of the solid polymer electrolysis element 1 can also be elongated by setting the upper limit of the electric current value to 0 to 8A, preferably 2 to 6A, and by feeding back the electric current value to the electric current source 7 through an electric current upper limit-controlling means 27, since the resistance value of the solid electrolyte membrane is 0.5 to 1 Ω at 23° C. and 50% RH which are the normal temperature environment.

Effect of Invention

The oxygen-concentrating equipment in the present invention can provide the equipment installed with the humidifying means which does not need periodic maintenance such as the supply of water, continuously gives a sufficient humidification degree, and can be set freely and easily with the humidification degree, especially the maintenance-free equipment not needing the maintenance of the humidifier by a patient of respiratory disease during the employment of the equipment. The oxygen-concentrating equipment in the present invention can also provide the equipment which is friendly for the patient, for example, with which the influence on the humidification degree by the employment environment on the humidification degree can be controlled with the employed electric current, its voltage or the like.

What is claimed is:

1. An oxygen-concentrating equipment comprising an oxygen-concentrating means for separating oxygen from air to concentrate the oxygen, a humidifying means for humidifying the oxygen-concentrated air produced by said oxygen-concentrating means, and an oxygen-supplying means for supplying the humidified oxygen-concentrated air to a user, characterized in that said humidifying means has at least a cation-conducting solid electrolyte membrane equipped with electrodes on both the sides of the membrane and an electric source for applying an electric current to said electrodes.

2. The oxygen-concentrating equipment according to claim 1, characterized in that said humidifying means is a means which has, on the anode side, a catalyst layer for electrolyzing water molecule into oxygen molecule and hydrogen ion and has, on the cathode side, a catalyst layer for producing water molecule from the oxygen molecule and the hydrogen ion.

3. The oxygen-concentrating equipment according to claim 2, characterized in that said oxygen-concentrating means is a pressure swing adsorption type oxygen-concentrating means which has an adsorption cylinder filled with an adsorbent adsorbing nitrogen more selectively than oxygen and a compressor for supplying compressed air to said adsorption cylinder, and said humidifying means has a flow path to flow raw material air, to be supplied to said compressor, on an anode side and a flow path to flow the oxygen-concentrated air, produced by said oxygen-concentrating means, on a cathode side.

4. The oxygen-concentrating equipment according to claim 2, characterized in that said oxygen-concentrating means is a pressure swing adsorption type oxygen-concentrating means which has an adsorption cylinder filled with an adsorbent adsorbing nitrogen more selectively than oxygen and a compressor for supplying compressed air to said adsorption cylinder, and said humidifying means has a flow path to flow cooling air on an anode for cooling the inside of said oxygen-concentrating equipment and a flow path to flow the oxygen-concentrated air, produced by said oxygen-concentrating means, on a cathode side for allowing.

5. The oxygen-concentrating equipment according to claim 2, characterized in that said oxygen-concentrating means is a pressure swing adsorption type oxygen-concentrating means which has an adsorption cylinder filled with an adsorbent adsorbing nitrogen more selectively than oxygen and a compressor for supplying compressed air to said adsorption cylinder, and said humidifying means has a flow path to flow the air desorbed from the adsorption cylinder on an anode side and a flow path to flow the oxygen-concentrated air, produced by said oxygen-concentrating means, on a cathode side.

6. The oxygen-concentrating equipment according to claim 1, characterized in that a control means, for controlling the electric current value and/or voltage value of an electric current applied from said electric source to said electrodes, is installed.

7. The oxygen-concentrating equipment according to claim 6, characterized in that a humidity-measuring means, on the cathode side of said humidifying means or in the downstream on the cathode side of said humidifying means, is installed and a control means, for controlling said measuring means so that the measurement value of said humidity-measuring means is equal to a set value, is installed.

8. The oxygen-concentrating equipment according to claim 6, characterized in that a control means, for calculating the transfer rate of water on the basis of the flow rate value and temperature value of the oxygen-concentrated air flowing on the cathode side of said humidifying means and then controlling said control means, is installed.

9. The oxygen-concentrating equipment according to claim 1, characterized in that a control means, for controlling the electric current value and/or voltage value of an electric current applied from said electric source to said electrodes so that the electric current value and/or voltage value do not exceed constant values or more, is installed.

* * * * *

Disclaimer 6,695,956 B2 — Masato Sugano, Tokyo (JP); Sadakazu Matsubara, Tokyo (JP); Satoshi Takaichi, Tokyo (JP). OXYGEN CONCENTRATING APPARATUS. Patent dated February 24, 2004. Disclaimer filed September 22, 2008, by the assignee, Teijin Limited.

Hereby enters this disclaimer to claims 1-9, of said patent.

*(Official Gazette October 21, 2008)*